US00PP12356P2

(12) United States Plant Patent
Ruigrok

(10) Patent No.: US PP12,356 P2
(45) Date of Patent: Jan. 15, 2002

(54) DAHLIA PLANT NAMED 'PICARDIE'

(76) Inventor: Frank N. G. Ruigrok, Hyacintenlaan 15, 2182 DE Hillegom (NL)

( * ) Notice: Subject to any disclaimer, the term of this patent is extended or adjusted under 35 U.S.C. 154(b) by 0 days.

(21) Appl. No.: 09/626,352

(22) Filed: Jul. 26, 2000

(30) Foreign Application Priority Data

Oct. 16, 1998 (EP) ..... 98/1390

(51) Int. Cl.[7] ..... A01H 5/00

(52) U.S. Cl. ..... Plt./321

(58) Field of Search ..... Plt./321

(56) References Cited

PUBLICATIONS

UPOV–ROM GTITM Computer Database, 2001/02, GTI Jouve Retrieval Software, citation for 'Picardie'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Dahlia plant named 'Picardie' characterized by its upright, uniformly mounded and compact plant habit; freely branching habit, full and dense plants; continuous and freely flowering during the spring until fall; full inflorescences with multiple rows of ray florets; bright yellow-clored ray florets with bright yellow-colored disc florets; and excellent garden and patio container performance.

1 Drawing Sheet

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the cultivar name Picardie.

The new Dahlia is a product of a planned breeding program conducted by the Inventor in Hillegom, The Netherlands. The objective of the breeding program is to create new pot-type Dahlia cultivars with desirable inflorescence form, attractive colors, and good garden performance.

The new Dahlia originated from a cross made by the Inventor in 1995 of two unidentified proprietary *Dahlia variabilis* seedling selections. The new Dahlia was discovered and selected by the Inventor as a single flowering plant within the progeny of the stated cross grown in a controlled environment in Hillegom, The Netherlands. The selection of this plant was based on its desirable inflorescence form and attractive floret colors.

Asexual reproduction of the new Dahlia by vegetative tip cuttings was first conducted in Hillegom, The Netherlands in 1996. Asexual reproduction by cuttings has shown that the unique features of this new Dahlia are stable and reproduced true to type in successive generations.

SUMMARY OF THE INVENTION

The cultivar Picardie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Picardie'. These characteristics in combination distinguish 'Picardie' as a new and distinct pot-type Dahlia:

1. Upright, uniformly mounded and compact plant habit.
2. Freely branching, full and dense plants.

3. Continuous and freely flowering during the spring until fall.
4. Full inflorescences with multiple rows of ray florets.
5. Bright yellow-colored ray florets with bright yellow-colored disc florets.
6. Excellent garden and patio container performance.

Plants of the new Dahlia differ from plants of the parent selections and Dahlia cultivars known to the Inventor primarily in ray floret coloration and its freely flowering habit.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which more accurately describe the actual colors of the new Dahlia. The photograph comprises a side perspective view of a typical flowering plant of 'Picardie'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the spring and summer in Keller, Tex., under outdoor conditions which approximate those generally used in commercial production. One rooted cutting was planted in a 12.5-cm container and pinched twice. Measurements and numerical values represent averages of typical flowering plants about 10 weeks after planting.

Botanical classification: *Dahlia variabilis* cultivar Picardie.
Commercial classification: Pot-type Dahlia.

Parentage:

*Female, or seed, parent.*—Proprietary *Dahlia variabilis* seedling selection, not patented.

*Male, or pollen, parent.*—Proprietary *Dahlia variabilis* seedling selection, not patented.

Propagation:

*Type.*—Terminal tip cuttings.

*Time to rooting.*—About seven to ten days with soil temperatures of 21° C.

*Root description.*—Fine, fibrous and well-branched; development of tubers has not been observed.

Plant description:

*Appearance.*—Herbaceous pot-type Dahlia. Inverted triangle; stems mostly upright and somewhat outwardly spreading giving a uniformly mounded appearance to the plant; relatively compact. Freely branching, lateral branches develop at every node after removal of terminal apex (pinching); dense and full plants. Vigorous.

*Plant height.*—To top of leaf plant: About 25 cm. To top of inflorescences plane: About 29.5 cm.

*Plant width or area of spread.*—About 30 cm.

*Lateral branches.*—Internode length: About 2.3 cm. Diameter: About 5 mm. Strength: Strong, very flexible. Texture: Very smooth, glabrous, glossy. Color: 146A.

*Foliage description.*—Arrangement: Leaves single or compound and trifoliate. Length: Compound leaves: About 3.8 cm. Terminal leaflet: About 3.4 cm. Single leaves: About 4 cm. Width: Compound leaves: About 4.2 cm. Terminal leaflet: About 2.1 cm. Single leaves: About 2.4 cm. Shape: Ovate. Apex: Acute to cuspidate. Base: Obtuse. Margin: Dentate with ciliation. Texture: Smooth, glabrous, leathery. Venation pattern: Pinnate. Color: Young foliage upper surface: 147A. Young foliage lower surface: 147B. Mature foliage upper surface: 147A. Mature foliage lower surface: Close to 147B. Venation, upper surface: Close to 147B. Venation, lower surface: Close to 147B to 147C. Petiole length: Compound leaves: About 2.1 cm. Single leaves: About 1.6 cm. Petiole diameter: Compound leaves: About 3 mm. Single leaves: About 2 mm. Petiole color: 146B to 146C.

Inflorescence description:

*Appearance.*—Terminal and axillary inflorescences held above the foliage on strong flexible peduncles. Composite inflorescence form with elongated oblong-shaped ray florets and disc florets massed at the center; ray and disc florets arranged acropetally on a capitulum. Not fragrant.

*Flowering response.*—Plants flower continuous and freely from the spring through the fall.

*Postproduction longevity.*—Inflorescences maintain good color and substance for about one or two weeks in an outdoor environment dependent on temperature.

*Quantity of inflorescences.*—About 32 open inflorescences and buds per plant.

*Inflorescence bud (just before opening).*—Shape: Spherical to ovoid. Height: About 8 mm. Diameter: About 6 mm. Color: Close to 154A.

*Inflorescence size.*—Diameter: About 3.2 cm. Depth (height): About 1.3 cm. Diameter of disc: About 1.1 cm.

*Ray florets.*—Shape: Elongated-oblong. Orientation: Initially upright, outer florets perpendicular to peduncle. Aspect: Straight, convex. Length: About 1.5 cm. Width: About 8 mm. Apex: Acute. Base: Attenuate; short corolla tube. Margin: Entire. Texture: Smooth, glabrous. Number of ray florets per inflorescence: About 32 in about two rows. Color: When opening, upper surface: Bright yellow, close to 9A. When opening, lower surface: Close to 9B. Fully opened, upper surface: Bright yellow, close to 9A. Fully opened, lower surface: Close to 9B.

*Disc florets.*—Shape: Tubular, elongated. Apex: Five-pointed. Length: About 5.5 mm. Width: Apex, about 1.5 mm; base, about 1 mm. Number of disc florets per inflorescence: About 66. Color: Immature: 154A. Mature: Apex: 9A. Base: 155D.

*Involucral bracts.*—Length: About 7 mm. Width: About 3.5 mm. Shape: Spatulate. Apex: Acute. Margin: Entire. Texture: Waxy, leathery, somewhat fleshy. Number per inflorescence: About 10 to 12. Color, both surfaces: 146A.

*Peduncles.*—Length, terminal inflorescence: About 3.8 cm. Diameter: About 2 mm. Strength: Strong, very flexible. Color: 144A.

*Reproductive organs.*—Androecium: Present on disc florets only. Number of stamens per floret: One. Stamen length: Less than 1 mm. Stamen color: White. Anther color: 9A to 12A. Pollen amount: Pollen production has not been observed. Gynoecium: Present on both ray and disc florets. Number of pistils per floret: One. Pistil length: Less than 1 mm. Color: Yellow.

*Seed production.*—Seed production has not been observed.

Disease resistance: Resistance to pathogens common to Dahlias has not been observed on plants grown under commercial greenhouse or outdoor conditions.

Weather tolerance: Plants of the new Dahlia have heen observed to be wind and rain-tolerant. Plants of the new Dahlia tolerant temperatures from 1° to 40° C.

It is claimed:

1. A new and distinct cultivar of Dahlia plant named 'Picardie', as illustrated and described.

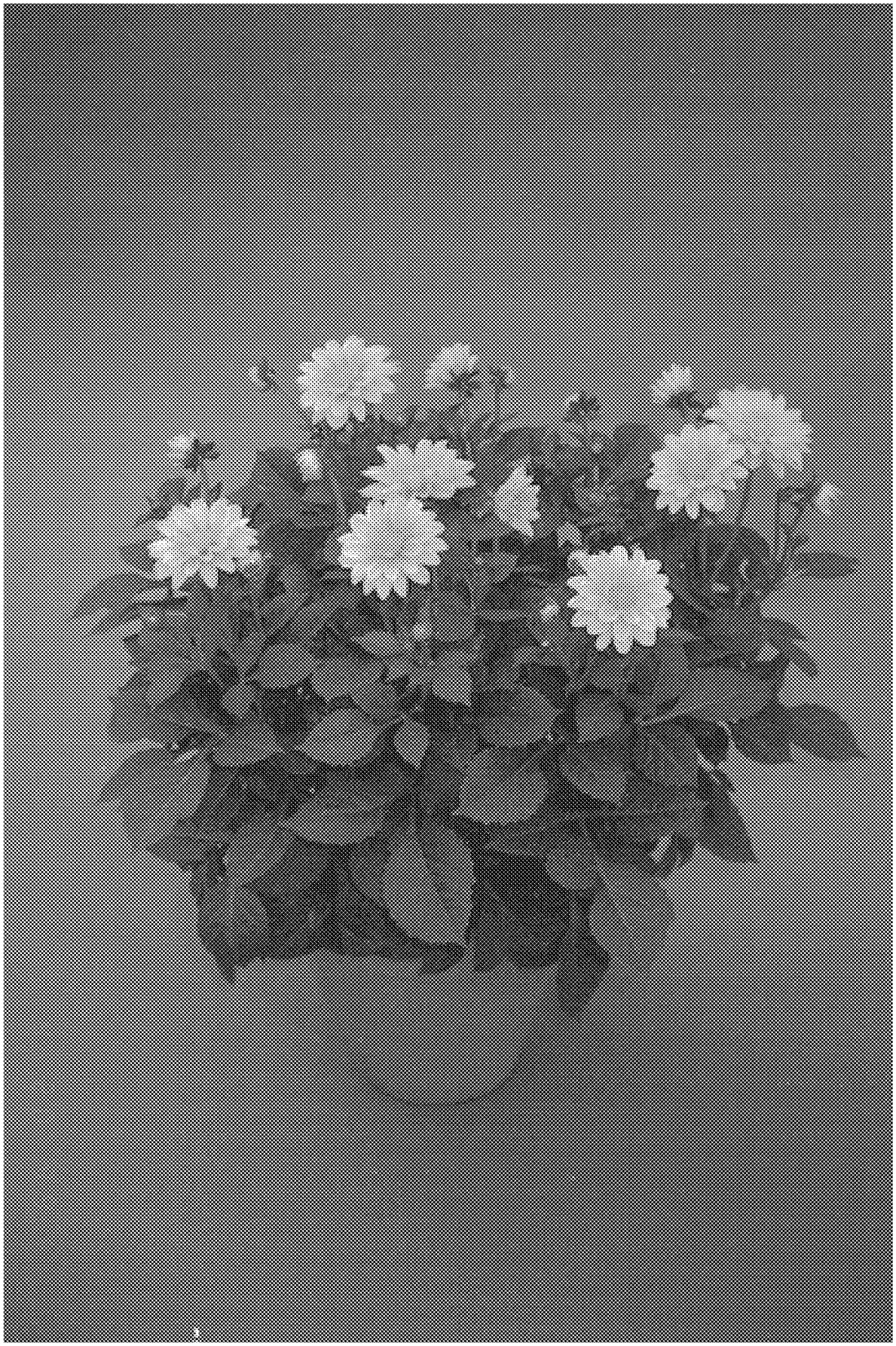

* * * * *